(12) United States Patent
Demers et al.

(10) Patent No.: US 10,893,874 B2
(45) Date of Patent: Jan. 19, 2021

(54) INSTRUMENTS AND METHODS FOR PREPARING A BONE TO RECEIVE A PROSTHESIS

(71) Applicant: Howmedica Osteonics Corp., Mahwah, NJ (US)

(72) Inventors: Matthew Demers, Ramsey, NJ (US); Fabiano Pace, Mahwah, NJ (US); Charles Jacob Shotmeyer, Franklin Lakes, NJ (US); Elena Steffan, Elma, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 251 days.

(21) Appl. No.: 15/998,464

(22) Filed: Aug. 15, 2018

(65) Prior Publication Data

US 2019/0076156 A1    Mar. 14, 2019

Related U.S. Application Data

(60) Provisional application No. 62/585,844, filed on Nov. 14, 2017, provisional application No. 62/545,631, filed on Aug. 15, 2017.

(51) Int. Cl.
*A61B 17/15* (2006.01)
*A61B 17/16* (2006.01)

(52) U.S. Cl.
CPC ........ *A61B 17/1668* (2013.01); *A61B 17/155* (2013.01); *A61B 17/157* (2013.01); *A61B 17/1666* (2013.01); *A61B 17/151* (2013.01)

(58) Field of Classification Search
CPC ............ A61B 17/1666; A61B 17/1668; A61B 17/151; A61B 17/154; A61B 17/155; A61B 17/157
USPC .......................................... 606/86 R, 87–89
See application file for complete search history.

(56) References Cited

U.S. PATENT DOCUMENTS

| 4,997,448 | A | 3/1991 | Filer |
| 5,089,004 | A | 2/1992 | Averill et al. |
| 5,169,402 | A | 12/1992 | Elloy |
| 5,507,832 | A | 4/1996 | Michielli et al. |
| 5,674,223 | A | 10/1997 | Cipolletti |
| 5,766,261 | A | 6/1998 | Neal et al. |
| 5,989,261 | A | 11/1999 | Walker et al. |
| 7,815,645 | B2 | 10/2010 | Haines |
| 7,837,690 | B2 | 11/2010 | Metzger |
| 8,361,159 | B2 | 1/2013 | Ek |
| 9,095,356 | B2 | 8/2015 | Thomas et al. |
| 9,113,918 | B2 | 8/2015 | Chaney et al. |
| 9,320,603 | B2 | 4/2016 | Lieberman et al. |
| 9,358,029 | B2 | 6/2016 | Sikora et al. |
| 9,402,637 | B2 | 8/2016 | Song |
| 9,445,907 | B2 | 9/2016 | Meridew et al. |

(Continued)

FOREIGN PATENT DOCUMENTS

GB        2323037 B    6/2001

*Primary Examiner* — Si Ming Ku
(74) *Attorney, Agent, or Firm* — Lerner, David, Littenberg, Krumholz & Mentlik, LLP

(57) ABSTRACT

A method of resecting an end of bone comprising inserting a cutting guide having a guide surface into a void in an end of bone such that the guide surface is beneath an end surface of the bone, and resecting the bone along the guide surface while the cutting guide remains disposed within the void in the end of the bone.

9 Claims, 13 Drawing Sheets

(56) References Cited

U.S. PATENT DOCUMENTS

| | | |
|---|---|---|
| 9,662,122 B2 | 5/2017 | Young |
| 2002/0016634 A1 | 2/2002 | Maroney et al. |
| 2007/0225821 A1 | 9/2007 | Reubelt et al. |
| 2013/0325019 A1* | 12/2013 | Thomas ............. A61B 17/1735 606/88 |
| 2014/0081411 A1 | 3/2014 | Lieberman et al. |
| 2014/0228846 A1* | 8/2014 | Roby ................. A61B 17/1659 606/79 |
| 2014/0276850 A1 | 9/2014 | Chaney et al. |
| 2015/0119892 A1 | 4/2015 | Witt et al. |
| 2015/0119893 A1 | 4/2015 | Witt |
| 2016/0331467 A1 | 11/2016 | Slamin et al. |
| 2017/0100134 A1 | 4/2017 | Sharp et al. |
| 2017/0164960 A1 | 6/2017 | Thomas et al. |

* cited by examiner

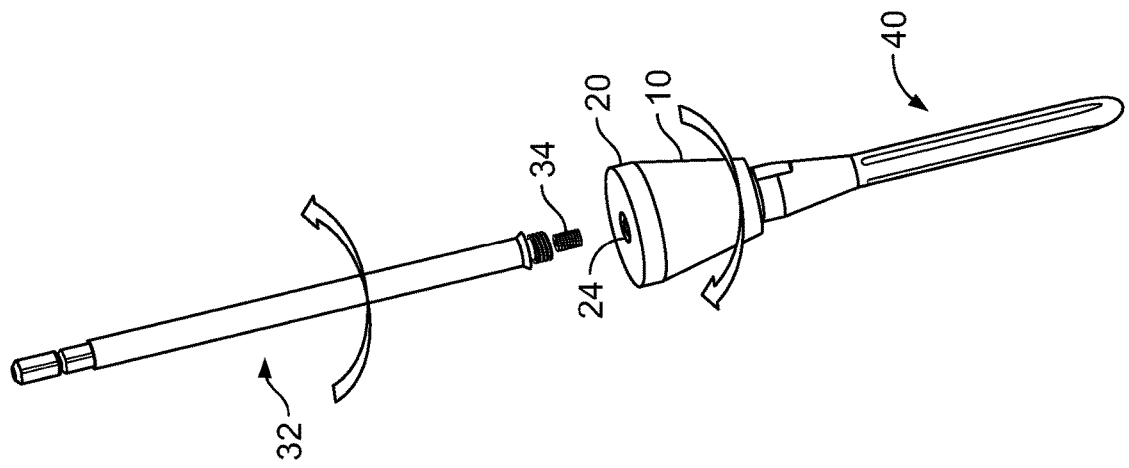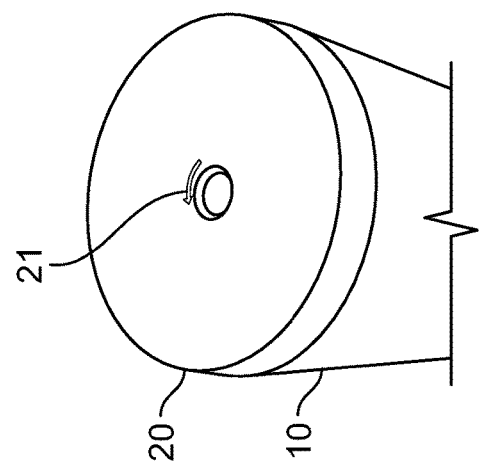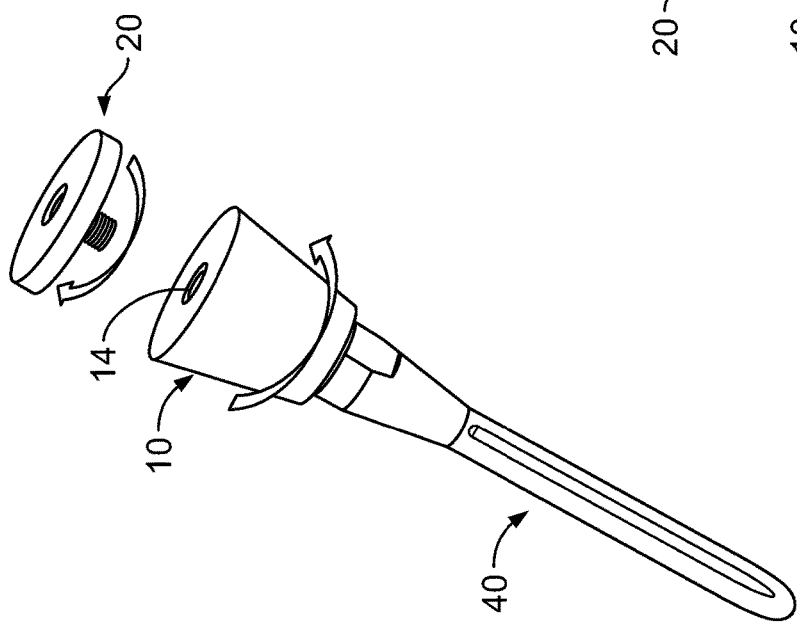

INSTRUMENTS AND METHODS FOR PREPARING A BONE TO RECEIVE A PROSTHESIS

CROSS-REFERENCE TO RELATED APPLICATIONS

This application claims the benefit of the filing dates of U.S. Provisional Application Nos. 62/545,631, filed on Aug. 15, 2017, and 62/585,844, filed on Nov. 14, 2017, the disclosures of which are hereby incorporated herein by reference.

BACKGROUND OF THE INVENTION

Joint replacement surgery is a common orthopedic procedure for joints such as the shoulder, hip, knee, ankle and wrist. Prior to implanting prosthetic components in a joint of a patient, a surgeon generally has to resect at least a portion of the patient's native bone in order to create a surface and/or recess or void for supporting, accepting or receiving at least a portion of the prosthetic components being implanted. Generally, a surgeon only resects the amount of bone that is needed in order to properly implant the prosthetic components in the joint because once native bone is resected from a joint, it is gone forever. Thus, the surgeon typically attempts to maintain as much of the native structural integrity of the joint as he or she can during the resection process.

When previously implanted prosthetic components fail for any one of a variety of reasons, a revision procedure is often necessary. An issue generally encountered by surgeons replacing joints during a revision procedure is the additional loss of native bone near the joint being replaced. This bone loss is typically due to movement of the component or components after implantation or even degeneration or further degeneration of the bone, which can form bone voids that have unpredictable and non-uniform shapes. In addition, revision procedures often involve the removal of additional bone, which makes maintaining or otherwise restoring the structural integrity often afforded by native bone of great importance.

For instance, when bone voids or deformities are observed in either the proximal tibia or distal femur, or both, it is standard surgical practice to fill those voids as part of the revision surgical procedure. The preferred practice is to fill those voids with weight bearing void fillers, typically made of an implant-grade metal such as titanium. However, because the bone voids are typically irregular in shape, some preparation of the bone void area is typically required prior to implantation of the void filler. This preparation (typically by reaming, broaching or milling) ensures there is sufficient room in the bone void for the void filler. An accurate fit between the shaped bone void and the void filler is also important for establishing joint line, and allowing for weight bearing and bone remodeling during the recovery process.

In addition to preparing a void to receive the void filler, an end of the bone is often resected to provide clean, even surfaces to interface with the joint implant. However, this is often made difficult in that the operator must consider the depth and angle of resection relative to the final placement of the void filler. In some circumstances, it is desirable for the void filler to be implanted so its end surface or surfaces are flush with the resected end of the bone. In other circumstances, it may be desirable for the void filler to be implanted beneath the end of the bone a predetermined distance. In either circumstance, the surgeon must be cognizant of the final placement of the void filler when performing the resection or risk misalignment of the bone and joint prosthesis with the void filler. There are currently few if any options for surgeons other than guesswork for performing such a resection. Therefore, further improvements are desirable.

BRIEF SUMMARY OF THE INVENTION

The present disclosure describes a resection guide system that allows a surgeon to make an accurate resection of an end of bone that takes into account a void filler's final placement. In this regard, the system that is described herein includes a resection guide body that has a shape and size corresponding to that of a void filler prosthesis and a resection guide shim that can be selectively connected to the resection guide body for accurate spacing relative to an end of the bone. Further, the system includes an inserter/extractor tool that may be used to place the guide body with or without the shim connected thereto into a prepared bone void. Methods of resecting an end of bone are also described herein in which the guide body with or without the shim is placed within a prepared bone void and utilized as an internal guide for a cutting instrument, such as a saw blade.

In one aspect of the present disclosure, a method of resecting an end of bone includes inserting a cutting guide having a guide surface into a void in an end of bone such that the guide surface is beneath an end surface of the bone; and resecting the bone along the guide surface while the cutting guide remains disposed within the void in the end of the bone.

Additionally, the method may include connecting a cutting guide shim to a cutting guide body to form the cutting guide. Also, the guide surface may be disposed on the cutting guide shim. The method may also include connecting the cutting guide shim to the cutting guide body before the cutting guide body is inserted into the void. Moreover, the method may include connecting the cutting guide shim to the cutting guide body after the cutting guide body is inserted into the void. Furthermore, the method may include removing the cutting guide from the bone void after the cutting step, and inserting a void filler prosthesis into the void.

In another aspect of the present disclosure, a method of preparing an end of bone to receive a prosthesis includes inserting a cutting guide having a cutting guide body and a cutting guide shim into a void in an end of bone; cutting the bone along a guide surface of the cutting guide shim while the cutting guide remains disposed within the void in the end of the bone so as to form a resected surface at the end of the bone; removing the cutting guide from the void; and implanting a void filler prosthesis into the void beneath the resected surface a distance equal to a thickness of the cutting guide shim.

Additionally, the cutting guide shim may be threadedly connected to the cutting guide body via a right-handed threaded interface. The cutting guide may be inserted into void via an inserter/extractor tool threadedly connected to the cutting guide shim. The inserter/extractor tool may be threadedly connected to the cutting guide shim via a left-handed threaded interface.

In an even further aspect of the present disclosure, a method of resecting bone, includes forming an opening at an end of a bone; driving a stabilizer device into the opening over a shaft extending from an end of the bone, the stabilizer having a size corresponding to a size of the opening such that the bone holds the stabilizer in position within the opening; placing a cutting guide over the shaft while the stabilizer device is positioned within the opening; and resecting the bone using the cutting guide.

Additionally, the method may include reaming an intramedullary canal of the bone using an intramedullary reamer, the intramedullary reamer comprising the shaft. Also, the forming step may include reaming the opening over the shaft of the intramedullary reamer. Moreover, the method may include sliding the stabilizer over the shaft such that the shaft is received within a through-opening of the stabilizer. The driving step may include sliding a seating instrument over the shaft and into contact with the stabilizer, and pushing the stabilizer into the opening via the seating instrument. The stabilizer may include a cannulated shaft with a flat end surface, and the sliding step may include bringing the flat end surface of the seating instrument into contact with a corresponding flat end surface of the stabilizer device. The opening may be conical and the stabilizer device may be cylindrical. However, the opening may be cylindrical and the stabilizer device may be cylindrical. However, the opening may also be conical and the stabilizer may also be conical.

BRIEF DESCRIPTION OF THE DRAWINGS

The features, aspects, and advantages of the present invention will become better understood with regard to the following description, appended claims, and accompanying drawings in which:

FIGS. 7A-7G illustrate a method of resecting an end of bone according to a further embodiment of the present disclosure.

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. Also, as used herein, the terms "about," "generally" and "substantially" are intended to mean that slight deviations from absolute are included within the scope of the term so modified.

Figure 1A:
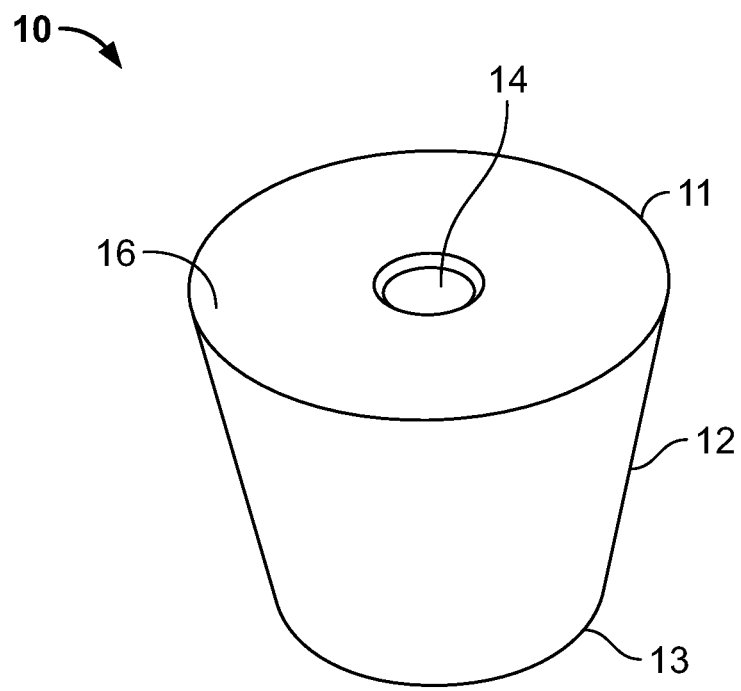
FIG. 1A is a perspective view of a resection guide body according to an embodiment of the present disclosure.
Figure 1B:
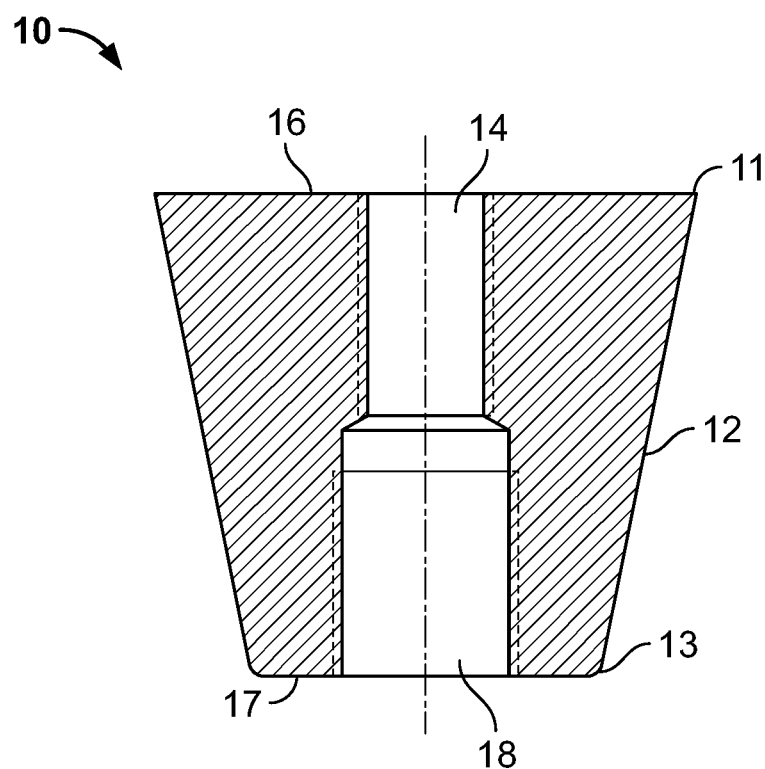
FIG. 1B is a cross-sectional view of the resection guide body of FIG. 1A taken along a midline thereof.

FIGS. 1A-3 depict a resection guide system which generally includes a resection guide body 10, resection guide shim 20, and inserter/extractor tool 30. The resection guide body 10, as best shown in FIGS. 1A and 1B, is shaped and sized to correspond to a void filler prosthesis (not shown). As depicted, resection guide body 10 is a tibial resection guide that is frustoconically shaped with a proximal end 11, a distal end 13, and a side surface 12 tapering inward from proximal end 11 to distal end 13. Such resection guide body 10 matches a void filler prosthesis with a similar geometry. However, it should be understood that while guide body 10 is depicted as a frustoconical device, it can be any number of different shapes and sizes provided it corresponds with the void filler prosthesis, which may be a void filler prosthesis for a multitude of different bones, such as a tibia, femur and the like. Examples of such void filler prostheses are disclosed in U.S. Pat. Nos. 9,011,444 ("the '444 Patent"); 9,149,282 ("the '282 Patent"); 9,526,513 ("the '513 Patent"); and 9,668,758 ("the '758 Patent"), the entireties of which are incorporated by reference herein and all of which are assigned to the same entity as the present invention.

Resection guide body 10 also includes a body guide surface 16 at proximal end 11 and a distal end surface 17. The body guide surface is substantially planar 16 and generally parallel to distal end surface 17. However, in some embodiments surface 16 may be sloped relative to surface 17. Body guide surface 16 is configured to act as a guide for a cutting instrument, such as a saw blade. In this regard, body guide surface 16 is a smooth surface made from a durable material, such as titanium, stainless steel, and the like. A proximal opening 14 extends through guide surface 16 while a distal opening 18 extends through distal end surface 17. Such openings 14, 18 are coaxial and intersect such so as to form a through-bore. The proximal opening 14 is internally threaded so as to threadedly mate with a right-hand screw 34 of inserter/extractor 30, and distal opening 18 is internally threaded so as to threadedly mate with a trial stem 40, as described in more detail below.

Figure 2A:
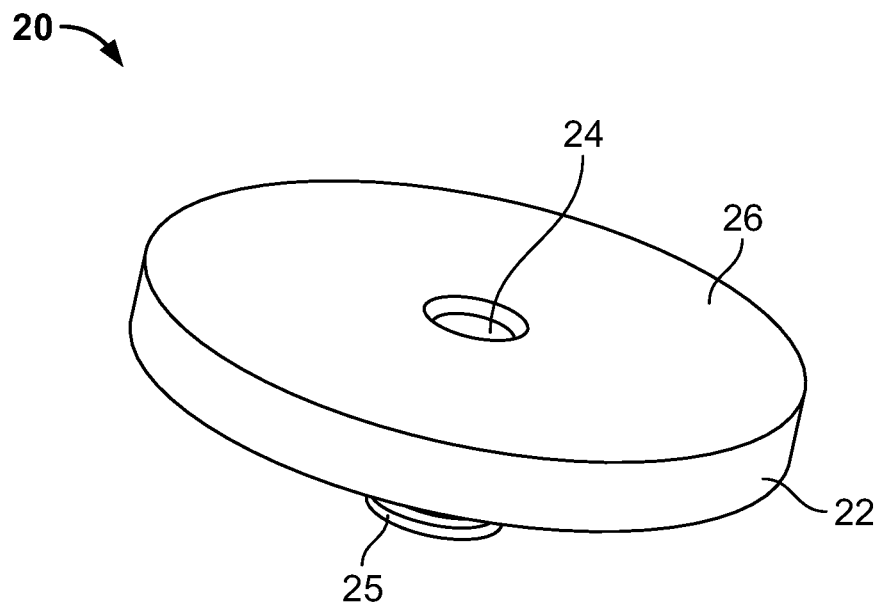
FIG. 2A is a perspective view of a resection guide shim according to an embodiment of the present disclosure.
Figure 2B:
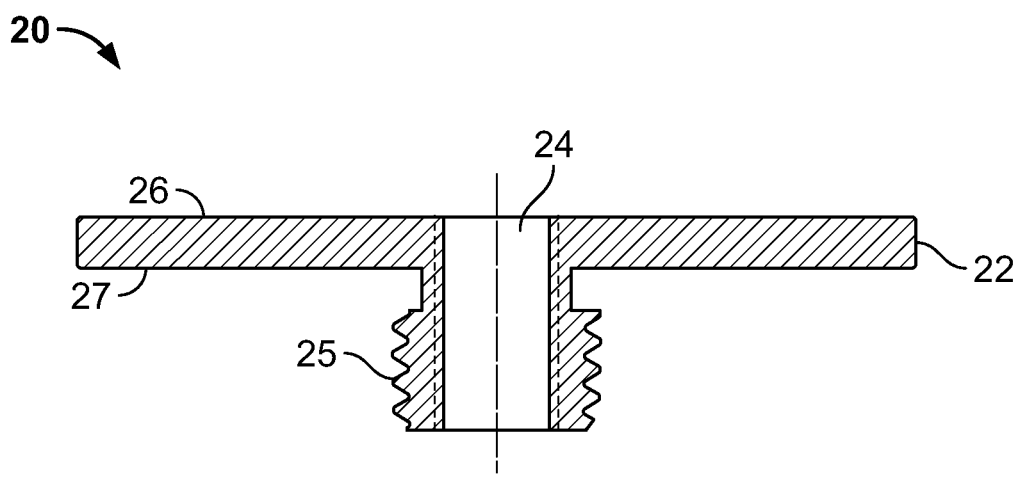
FIG. 2B is a cross-sectional view of the resection guide shim of FIG. 2A taken along a midline thereof.

As depicted in FIGS. 2A and 2B, resection guide shim 20 includes a shim guide surface 26, distal end surface 27, and side surface 22 extending therebetween. In addition, a threaded projection 25 extends from distal end surface 27. Threaded projection 25 is externally threaded with a right-handed thread which is configured to threadedly mate with the internal threads of proximal opening 14 of resection guide body 10. An opening 24 extends through shim guide surface 26 and into or through threaded projection 25. Such opening 24 is internally threaded with a left-handed thread which is configured to threadedly mate with a left-hand screw 36 of inserter/extractor 30, described below. Resection guide shim 20 has a diameter equivalent to a diameter of the resection guide body 10 at its proximal end. Thus, connecting resection guide shim 20 to resection guide body 10 extends the length of resection guide shim 10, but not its girth.

Shim guide surface 26 is similar to body guide surface 16 in that it is planar and configured to guide a cutting instrument as it resects an end of bone. In some embodiments, shim guide surface 26 may be parallel to distal end surface 27. In other embodiments, shim guide surface 26 may be angled relative to distal end surface 27. For example, shim guide surface 26 may be sloped 1 to 10 degrees relative to the distal end surface 27. This may allow a surgeon to apply a desired varus/valgus or anterior/posterior slope angle to an end of bone, as is described in more detail below.

Figure 3:
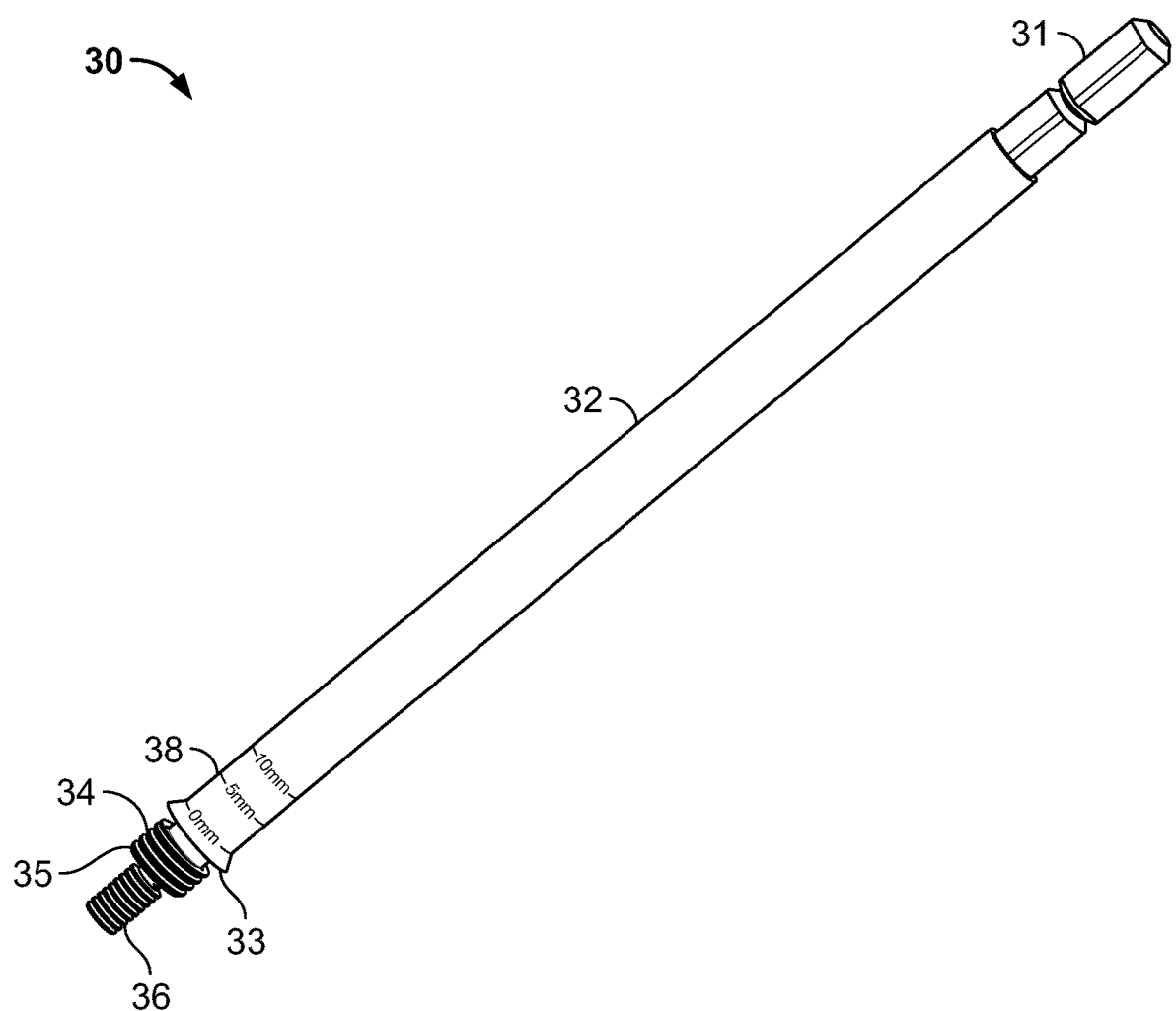
FIG. 3 is a perspective view of an inserter/distractor tool according to an embodiment of the present disclosure.

As depicted in FIG. 3, inserter/distractor tool 30 includes a shaft 32 with a proximal end 31 and a distal end. Proximal end 31 is configured to connect to other tools or devices, such as a T-handle, for example. The distal end is configured to connect to resection guide body 10 and resection guide shim 20. In this regard, a right-hand screw 34 extends distally from shaft 32, and a left-hand screw 36 extends distally from right-hand screw 34. A first shoulder 33 is formed between shaft 32 and right-hand screw 34. Similarly, a second shoulder 35 is formed between right-hand screw 34 and left-hand screw 36 as left-hand screw 36 has a smaller diameter than right-hand screw 34. Indicia 38 are located on shaft 32 adjacent right-hand screw 34. Such indicia 38 may be used as a depth indicator, as is describe further below.

Figure 4:
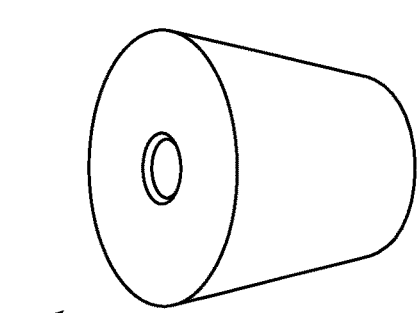
FIGS. 4 and 5 illustrate components of a kit according to an embodiment of the present disclosure.
Figure 4:
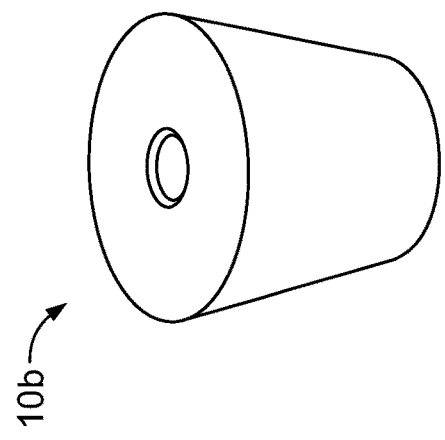
Figure 4:
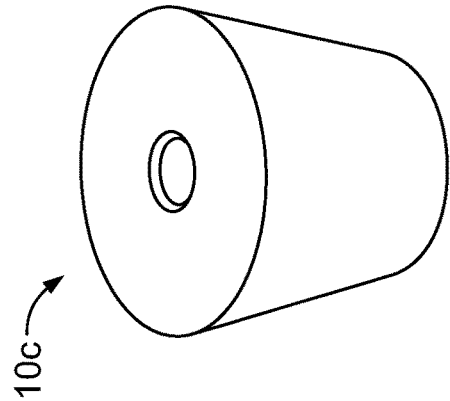
Figure 5:
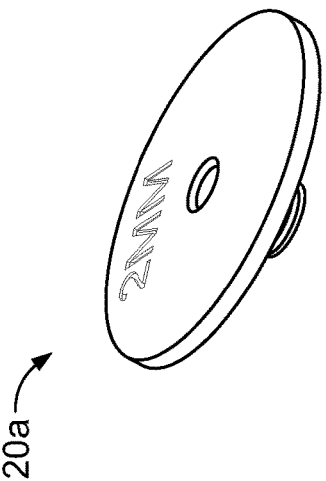
Figure 5:
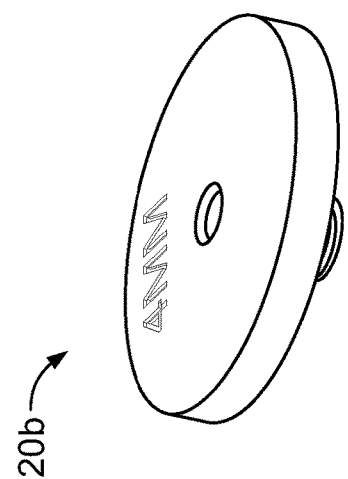
Figure 5:
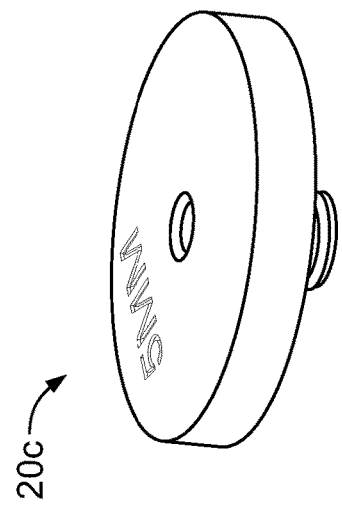

FIGS. 4 and 5 depict components of a kit which may include a plurality of resection guide bodies 10a-c and a plurality of resection guide shims 20a-c. Resection guide bodies 10a-c may each differ in size in order to accommodate different sized bone voids. In this regard, each of guide bodies 10a-c may have different cross-sectional dimensions. Thus, each guide body 10a-c may have a plurality of correspondingly dimensioned guide shims 20 associated with that guide body 10. For example, guide shims 20a-c may be associated with guide body 10a as guide shims 20a-c may have similar cross-sectional dimensions. As shown, each guide shim 20a-c differs in thickness, which may be in increments of 1 to 2 mm. In addition, several guide shims 20 with the same thickness may be provided. However, such same thickness guide shims 20 may have different sloped guide surfaces 26. For example, four 2 mm thick guide shims 20a may be provided where first, second, third, and fourth 2 mm guide shims have respective 0, 1, 2, and 3 degree slopes. Thus, during a procedure, the surgeon can select whichever guide body 10 and guide shim 20 is needed for the particular patient's anatomy.

FIGS. 6A-6H depict a method of resecting an end of bone according to an embodiment of the present disclosure. As shown, this method is performed on a tibia 50. However, it should be understood that such method is applicable to other bones that comprise a joint, such as a femur. This method may be performed when it is desired to have an end of the void filler flush when an end of bone 50. This may be indicated when bone stock at the end of bone 50 is deteriorated and in need of support. Thus, in the depicted method, a proximal tibia is resected to correspond with a void filler thereof. However, as suggested above, the following methods can also be performed to resect a distal femur to correspond with a void filler thereof.

In the method, a previously implant prosthesis is removed from bone 50. A defect at the end of bone 50 is assessed and prepared for a void filler. In this regard, a reamer, broach, or the like may be used to form a void for receipt of the void filler. Examples of methods and devices for preparing a void for a void filler can be found in the heretofore referenced patents incorporated by reference herein.

Figure 6B:
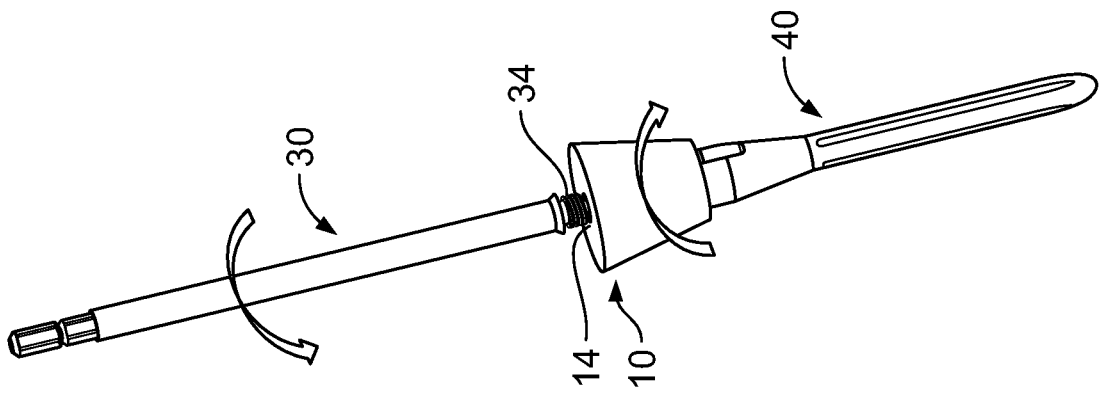
FIGS. 6A-6H illustrate a method of resecting an end of bone according to an embodiment of the present disclosure.
Figure 6A:
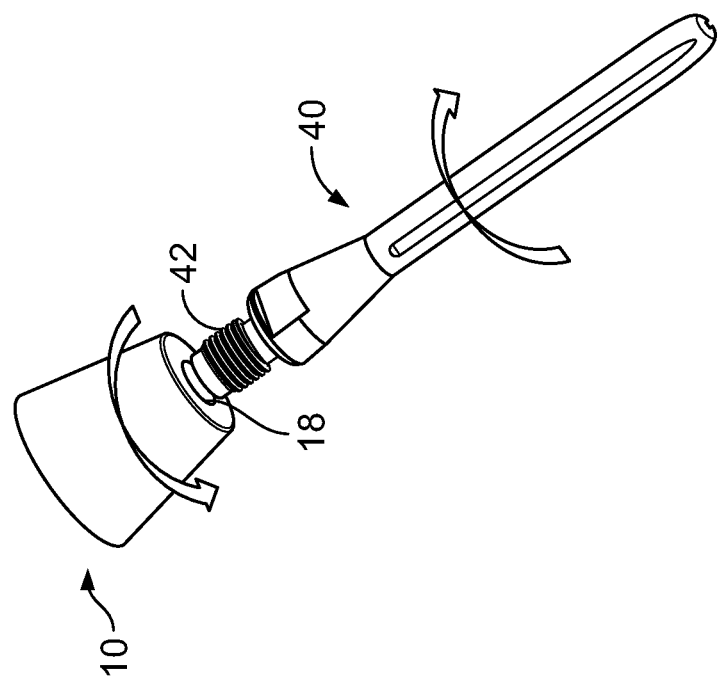

Thereafter, resection guide body 10 may be threaded to a proximal end 42 of the trial stem 40, as shown in FIG. 6A. Inserter/extractor 30 may then be threaded to resection guide body 10, as shown in FIG. 6B, by threading right-hand screw 34 of inserter extractor 30 into proximal opening 14 of guide body 10 until body guide surface 16 abuts first shoulder 33. A T-handle 39 may also be connected to proximal end 31 of inserter/extractor 30.

Figures 6C, 6D:
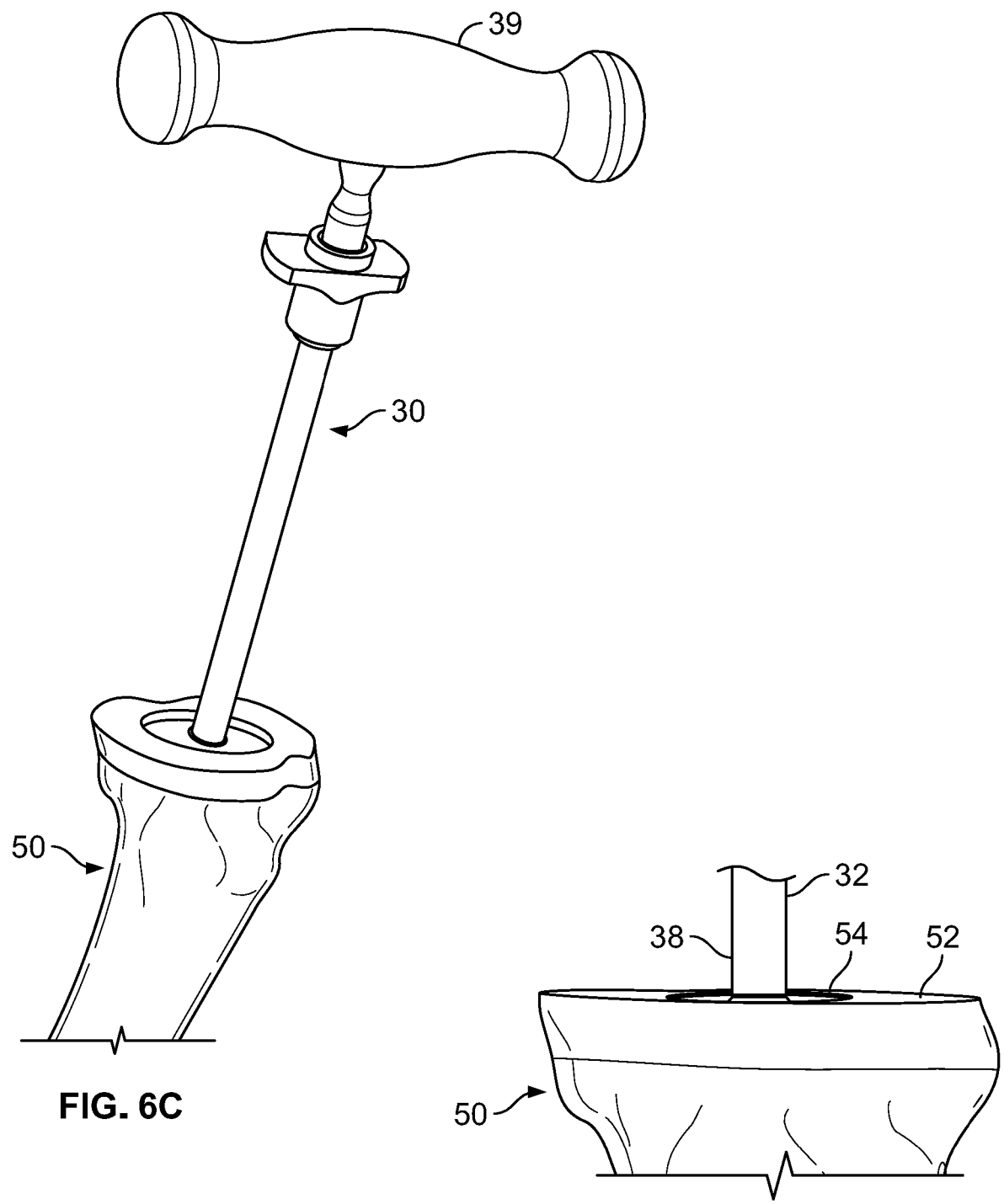

Trial stem 40 and resection guide body 10 are then inserted into the bone 50 via inserter/extractor 30 such that body guide surface 16 is disposed beneath an end surface 52 of the bone 50, as best shown in FIGS. 6C and 6D. It should be noted that such end surface 52 of bone 50 may have been resected in a previous procedure and is therefore referred to herein as first resected surface 52. At this point, trial stem 40 is disposed within the intramedullary canal and resection guide body 10 is positioned within the void previously formed for the void filler. Also, first resected surface 52 aligns with indicia 38 on shaft 32 indicating a distance between first resected surface 52 and body guide surface 16. In this regard, indicia 38 indicates a thickness of bone 50 to be removed so that the bone 50 is flush with body guide surface 26 and consequently a void filler when implanted in its final position.

Figure 6E:
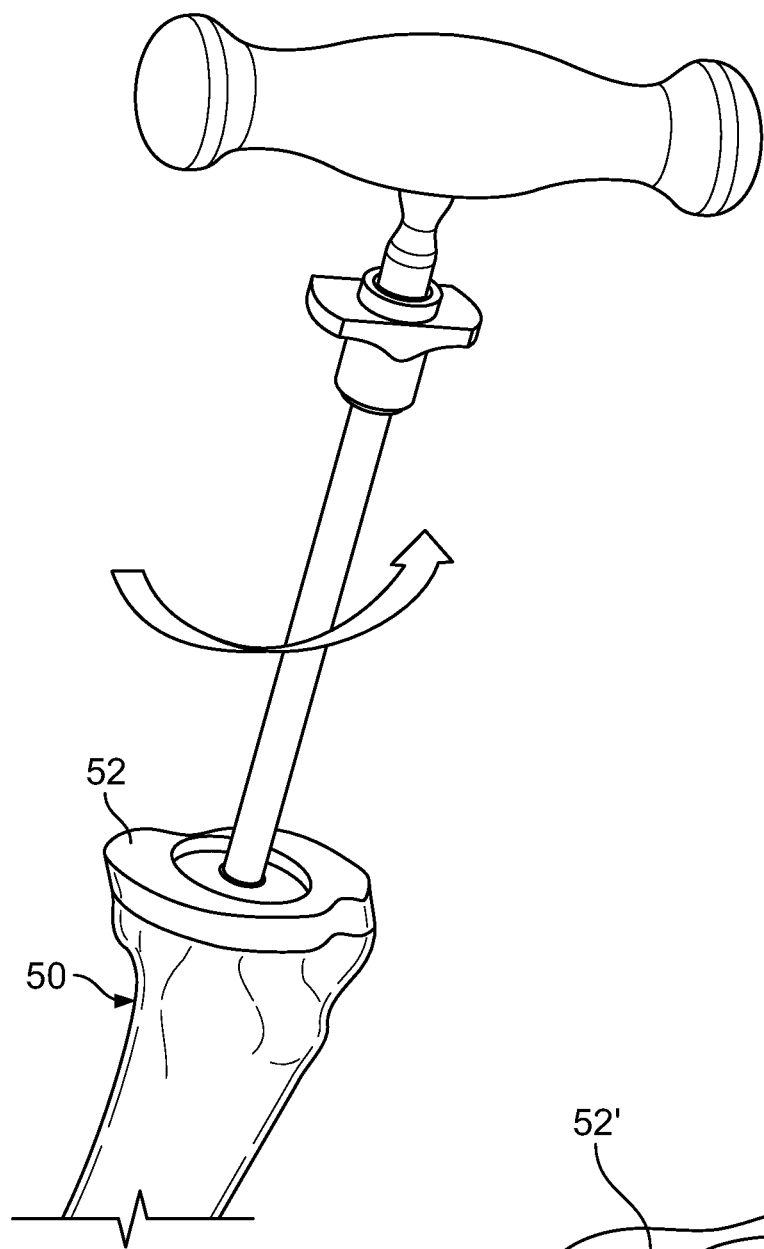
Figure 6F:
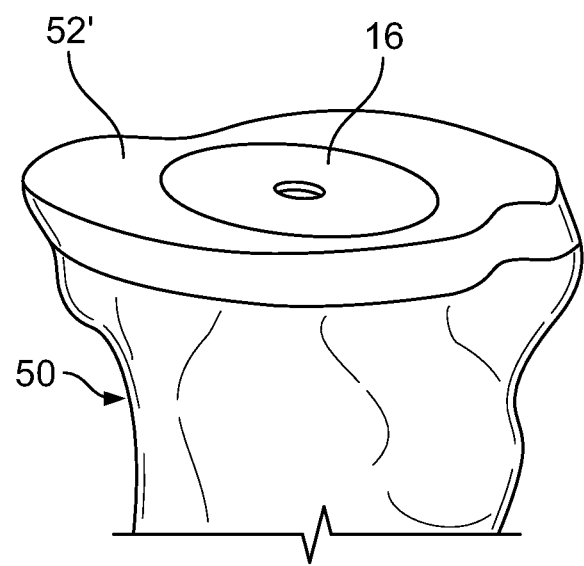
Figure 6G:
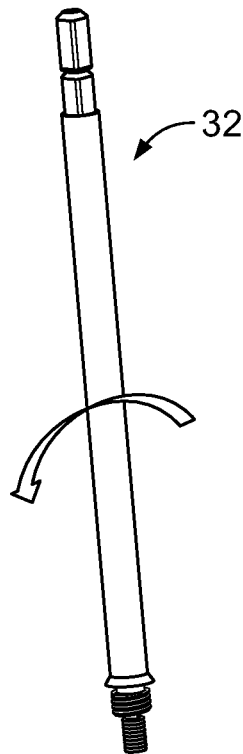
Figure 6G:
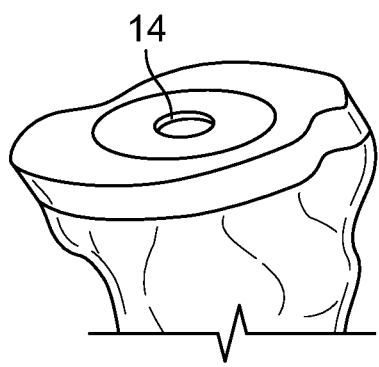
Figure 6H:
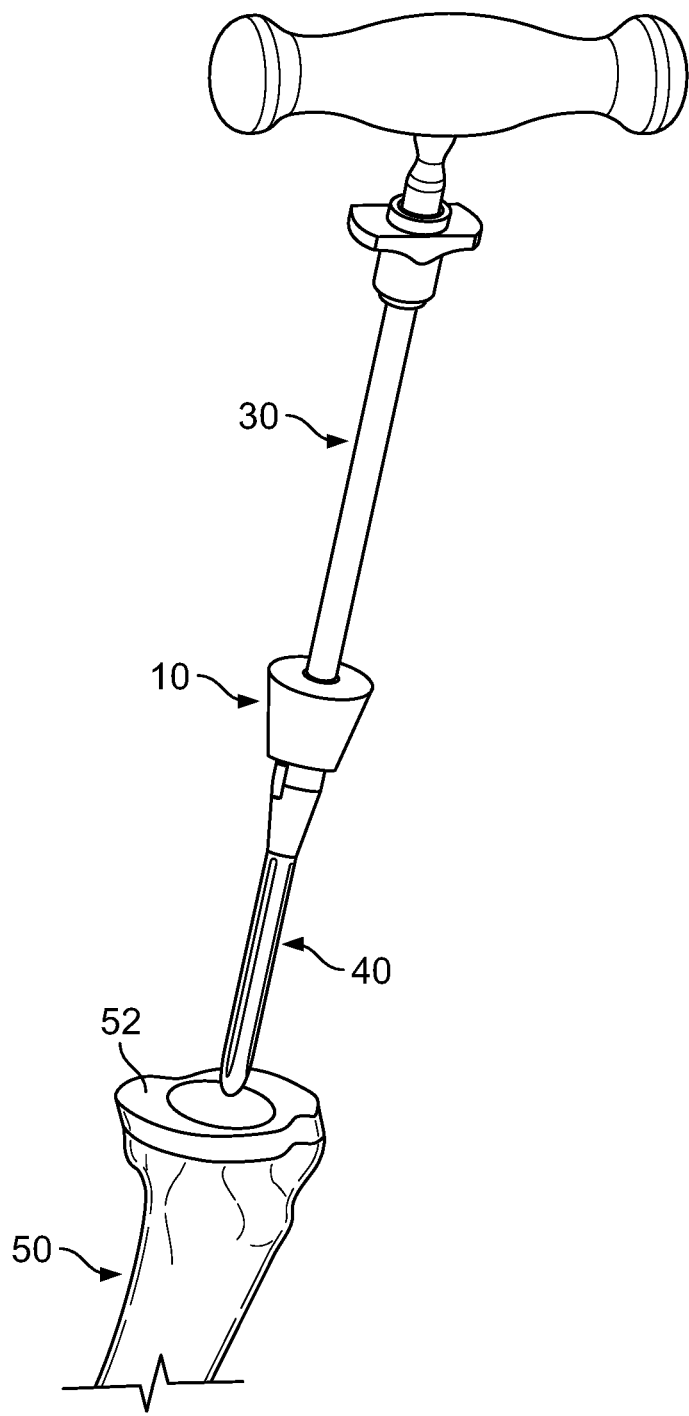

Once guide body 10 is properly seated in bone 50, inserter/extractor 30 is removed from proximal opening 14 of resection guide body 10 by rotating it counterclockwise, as shown in FIG. 6E. At this point, resection guide body 10 remains positioned in bone 50. Thereafter, a cutting instrument, such as a saw blade, is used to resect the portion 54 of bone 50 previously identified as spanning between first resected surface 52 and body guide surface 16. Body guide surface 16 acts as an internal guide surface to help the surgeon resect bone 50 so as to form a second resected surface 52' co-planar with body guide surface 16, as best shown in FIG. 6F. Thus, as the cutting devices cuts through bone 50, the cutting device can run along guide surface 16 without concern of over-resection.

Once bone 50 is resected, inserter/extractor 30 is reconnected to resection guide body 10 in the same manner previously described, and resection guide body 10 and stem 40 are extracted from bone 50. Thereafter, a void filler (not shown) may be press-fit or otherwise placed into the void in the end of bone 50. At this point the proximal end of the void filler should be flush with second resected surface 52'. A joint implant is then connected to the end of the bone including the void filler and second resected surface 52'.

FIGS. 7A-7G depict a method of resecting an end of bone 50 according to an alternative embodiment of the present disclosure. This method may be performed when it is desirable for the void filler prosthesis to be finally implanted entirely beneath the end of the bone 50 such that a portion of bone extends between the void filler and a resected end of the bone. This may be indicated where healthy bone stock is present at the end of bone 50 but additional support is needed within the metaphysis.

This method is similar to the method of FIGS. 6A-6H in that a previously implanted prosthesis is removed from an end of bone 50 and a void is prepared to receive a void filler prosthesis. However, unlike the previously described method, resection guide body 10 is connected to the trial stem 40 and resection guide shim 20 is connected to proximal end 11 of the resection guide body 10, as shown in FIG. 7A. In this regard, threaded projection 25 is inserted into proximal opening 14 and rotated clockwise until distal surface 27 of shim 20 is seated against body guide surface 16. As previously described, multiple guide shims 20 may be provided with different thicknesses and different slopes for varus/valgus and/or posterior slope alignment. Thus, the guide shim may be selected based upon the desired depth of resection and the angle of the resection.

Figures 7D, 7E:
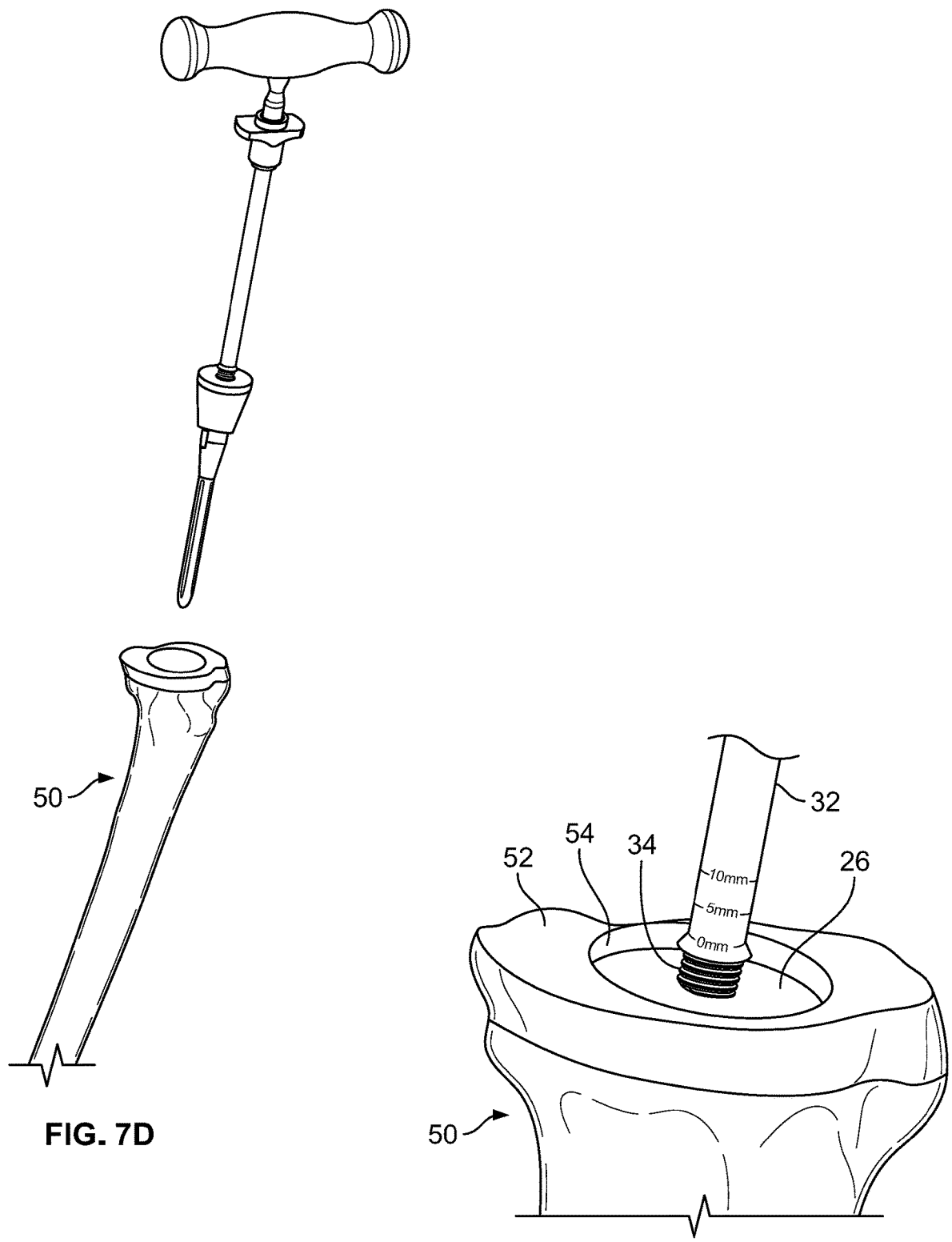

Thereafter, inserter/extractor 30 is connected to shim 20. As illustrated in FIG. 7C, left-hand screw 36 is inserted into opening 24 and rotated counterclockwise until second shoulder 35 seats against shim guide surface 26 (best shown in FIG. 7E). An indicator marking 21, such as an arrow, is located on shim guide surface 26 and indicates that the direction of rotation of inserter/extractor 10 is counterclockwise, as best shown in FIG. 7B.

Once inserter/extractor 30, guide body 10, guide shim 20, and trial stem 40 are assembled, the assembly is inserted into an end of bone 50 such that stem 40 is positioned within the intramedullary canal, and guide body 10 and shim 20 are positioned within the prepared bone void, as illustrated in FIGS. 7D and 7E. In this position, a portion 54 of bone 50 extends between first resected surface 52 of bone 50 and shim guide surface 26, as best shown in FIG. 7E. Thereafter, portion 54 of bone is assessed to determine if a thicker or thinner shim 20 is needed. A thicker shim 20 would result in less bone resected from the end of tibia 50 and a larger distance between the resected end of tibia 50 and an implanted void filler prosthesis. Conversely, a thinner shim 20 would result in more bone resected from the proximal end of tibia 50 and less distance between the resected end of the tibia 50 and an implanted void filler prosthesis. Such assessment may be based on the condition of the bone at the proximal end of tibia 50. If a different guide shim 20 is desired, inserter/extractor 30 can be rotated counterclockwise while guide shim 20 and guide body 10 are positioned within bone 50. The opposite handed threading of left-hand screw 36 of inserter/extractor 30 allows shim 20 to be unthreaded from guide body 10 and removed from the end of bone 50. Thereafter, a thicker or thinner guide shim 20 can be connected to inserter/extractor 30, inserted into the end of bone 50, and connected to guide body 10 within bone 50. A further assessment may then be made to determine if a further swap of shim guides is necessary.

Figure 7F:
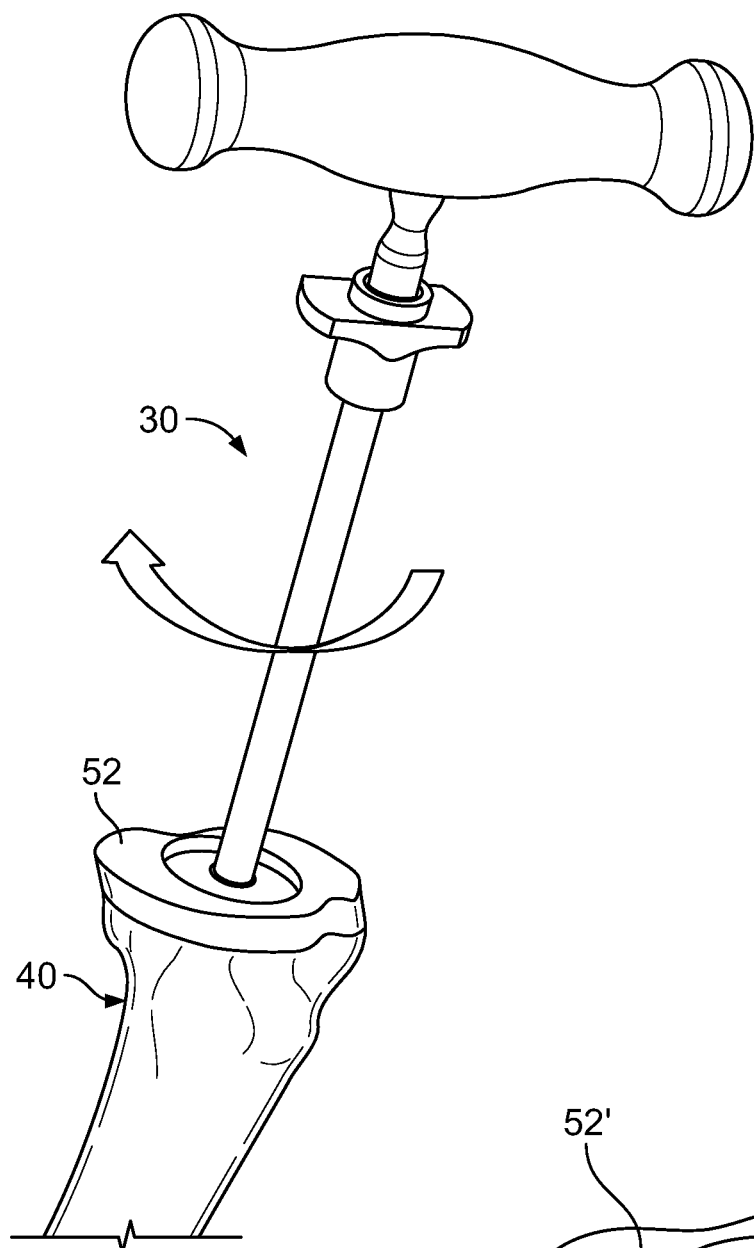
Figure 7G:
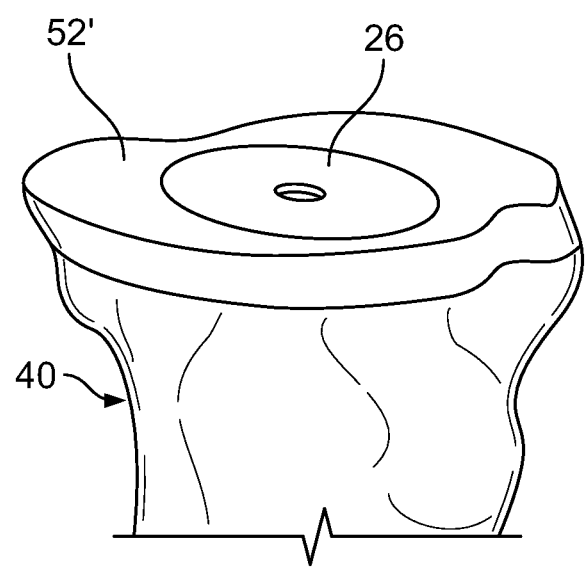

Once guide body 10 is properly seated with the appropriate guide shim 20, inserter/extractor 30 is removed from guide shim 20 by rotating it clockwise, as illustrated in FIG. 7F. Because guide shim 20 and guide body 10 are connected via a right-handed threaded connection, this clockwise disconnection of inserter/extractor 30 from guide shim 20 does not loosen the connection between guide shim 20 and guide body 10. Thus, the left-handed threaded connection between inserter/extractor 30 and guide shim 20 helps prevent inadvertent axial movement between shim guide 20 and guide body 10 during removal of inserter/extractor 30 from shim guide 20 which could result in the resection being too shallow.

Once the inserter/extractor 30 is removed, the portion 54 of bone at the end of tibia is resected using shim guide surface 26 as a guide for the cutting instrument such that the second resected surface 52' is coplanar with shim guide surface 26. If guide shim 20 has a sloped guide surface 26, then second resected surface 52' will reflect this slope. Thereafter, inserter/extractor 30 is connected to guide shim 20 and the entire assembly is extracted from bone 50. A void filler prosthesis may then be inserted into the void. Due to the use of guide shim 20 when performing the resection, the void filler will be seated below second resected surface 52' a distance reflected by the thickness of the guide shim. A joint prosthesis may then be implanted.

Although guide body 10 and guide shim 20 have been described herein as trials and cutting guides for the resection of an end of bone 50, guide body 10 and guide shim 20 can also be configured as broaches. For example, side surfaces 12 and 22 of guide body 10 and guide shim 20, respectively, can have cutting edges as would a conventional broach. This would allow for the total reduction of instruments in the operating room as a surgeon could use guide body 10 and guide shim 20 as preparation instruments to further refine the void to receive a void filler and as cutting guides for a clean-up resection of bone 50.

When performing a total knee arthroplasty, it is common for various resection instruments known in the art, such as a distal resection guide and a 4-in-1 cutting block, to be connected to a stem/shaft extending from an intramedullary canal of a bone. Such stem/shaft may align with an axis of the bone so as to create an anatomical reference for the resection instrumentation. When performing a revision procedure or other procedure involving the use of void filling implants due to excessive bone loss or degeneration, there may not be sufficient bone surrounding the stem/shaft to stabilize the stem/shaft from excessive movement. Such movement of the stem/shaft can result in inaccurate resections.

Figure 8:
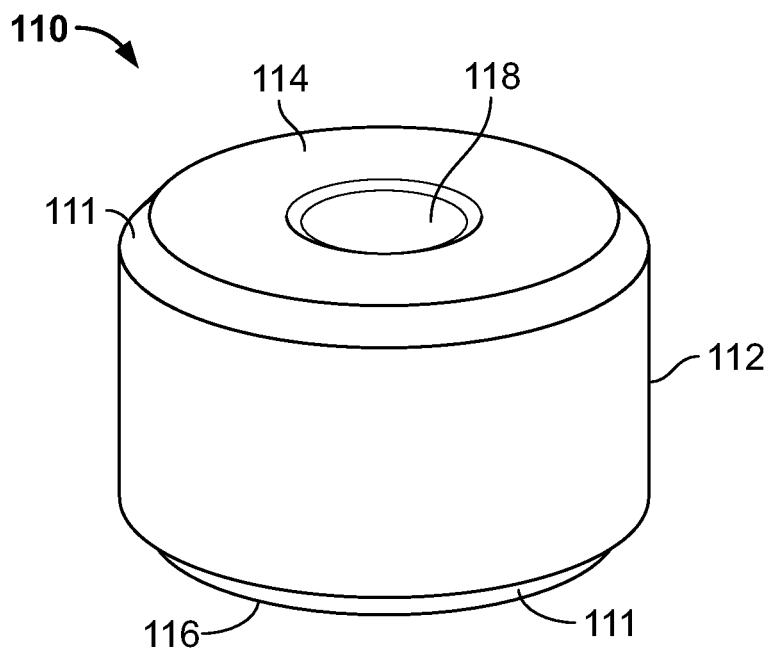
FIG. 8 is a perspective view of a stabilizer device according to an embodiment of the present disclosure.

FIG. 8 depicts a stabilizer device 110 that can be used to stabilize a stem/shaft 132 (see e.g., FIG. 10A) from excessive movement. Moreover, stabilizer 110 can center shaft/stem 132 within a bone so that it aligns with an axis of the bone. Stabilizer 110 includes a body which has first and second planar end surfaces 114, 116. A cylindrical exterior sidewall surface 112 extends between planar end surfaces 114, 116 giving stabilizer 110 a cylindrical profile. A chamfered edge 111 may connect each end surface 114, 116 with sidewall surface 112 in order to reduce sharp edges. In some embodiment, the diameter of stabilizer 110 is equal to or greater than a length of stabilizer 110. However, in some embodiments the diameter is smaller than the length of stabilizer 110. A through-hole 118 extends through stabilizer 110 from first end 114 to second end 116. A diameter of through-hole 118 is selected such that it is slightly larger than a diameter of shaft/stem 132 so that when stem/shaft 132 is received within hole 118, stabilizer 110 can only move rotationally about and translationally along stem/shaft 132.

Although stabilizer 110 is depicted as being cylindrical in shape with planar end surfaces 114, 116, stabilizer 110 can have many different shapes and configurations. The cylindrical shape shown is preferable as it fits easily within a reamed opening within a bone, which is often cylindrical or conical. However, the shape of stabilizer 110 can be any shape as long as such shape corresponds to a shape of a bone void within a bone and tightly fits against the bone in multiple directions. For example, stabilizer 110 may have a conical, frustoconical, oval or rectangular shape that corresponds to a respective opening in the bone. Such bone opening may be pre-formed to correspond to the dimensions of stabilizer 110.

In addition, stabilizer 110 may have conically tapered end surfaces that may taper inwardly toward a center of stabilizer 110 rather than having planar end surfaces 114, 116. In this regard, end surfaces 114, 116 can have may different configurations, but it is preferable that the configuration selected corresponds to an end of a seating instrument so that a uniform force can be applied to stabilizer 110 via the seating instrument, as is described below.

Figure 9:
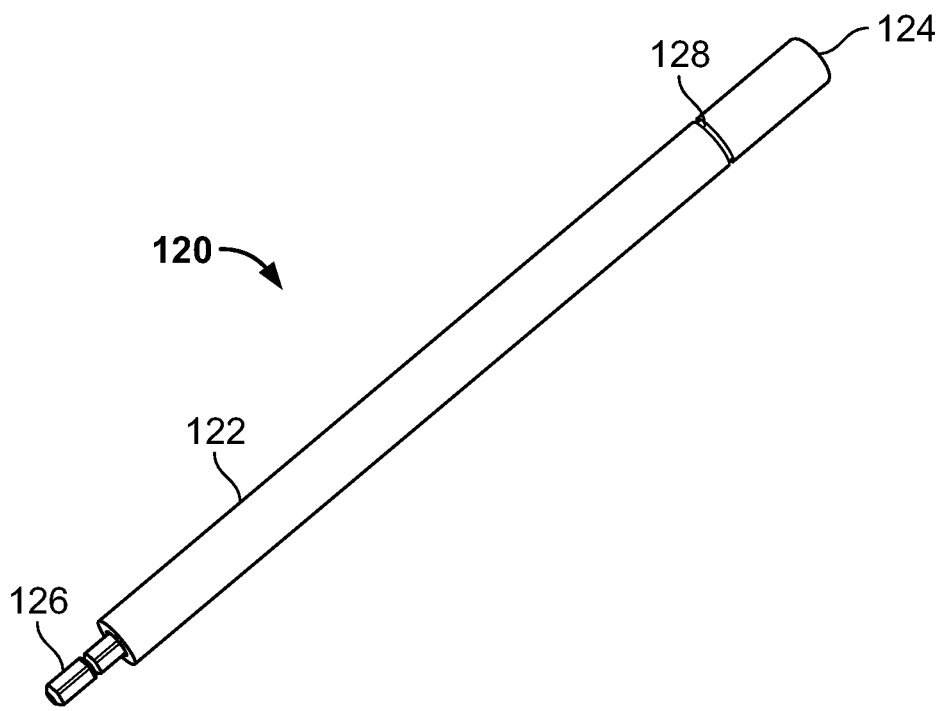
FIG. 9 is a perspective view of a seating instrument according to an embodiment of the present disclosure.

FIG. 9 depicts a seating instrument 120. Seating instrument 120 helps seat stabilizer 110 in an opening within a bone. Seating instrument 120, as shown, includes a cannulated shaft 122 with a seating end 124 and a connection end 126. Seating end 124 has a planar/flat end surface that is perpendicular to a longitudinal axis of shaft 122 and that corresponds to the flat end surfaces of stabilizer. In this regard, seating end 124 may have other configurations which correspond to the configuration of stabilizer 110. For example, where ends 114 and 116 of stabilizer 110 are conically tapered, seating end 124 may be correspondingly conically tapered so as to form a female-male conical interface. Seating end 124 also defines an opening that extends into the shaft. Connection end 126 is configured for connection to other components, such as a T-handle, such as the one shown in FIG. 10B, for example. Indicia 128 may be included on shaft 122 near seating end 124. Such indicia 128 are located along shaft 122 to indicate a seating depth of stabilizer 110.

The above described stabilizer 110 and seating instrument 120 may be provided in a kit. For example, one kit may include a plurality of stabilizers 110 each with a different diameter to accommodate different sized bone openings and a seating instrument 120 which may universally fit each of the stabilizers 110. Such kit may also include a plurality of reamers including an intramedullary reamer for reaming an intramedullary canal of a bone and a void reamer for reaming an opening in an end of the bone for the stabilizer. Examples of such reamers are described in the heretofore referenced patents, such as the '444, '282, '513 and '758 Patents, which again, are incorporated by reference herein.

Figure 10A:
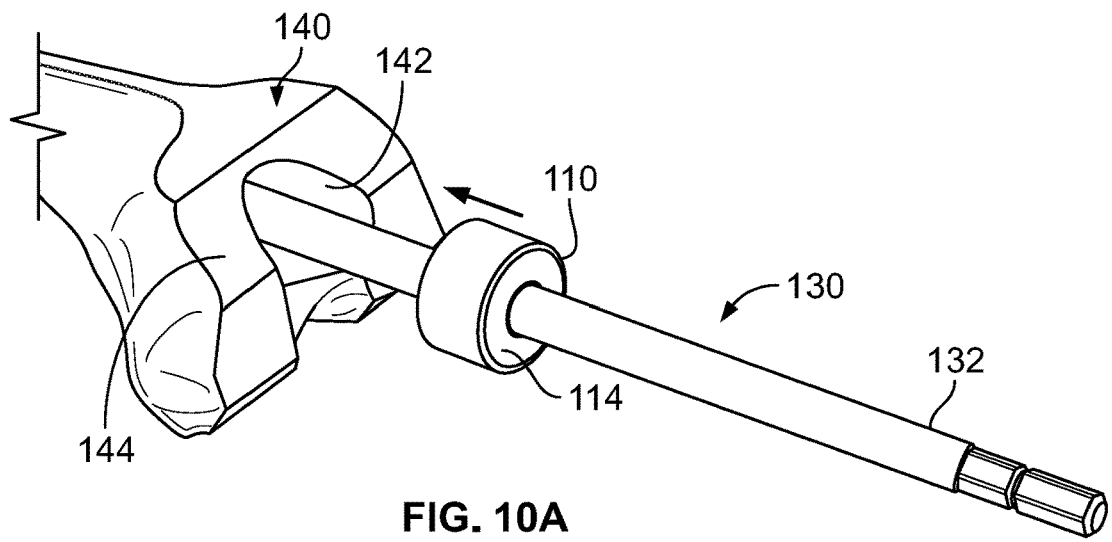
FIGS. 10A-10C illustrate a method of using the stabilizer and seating instrument of FIGS. 8 and 9, respectively, in accordance with an embodiment of the present disclosure.
Figure 10B:
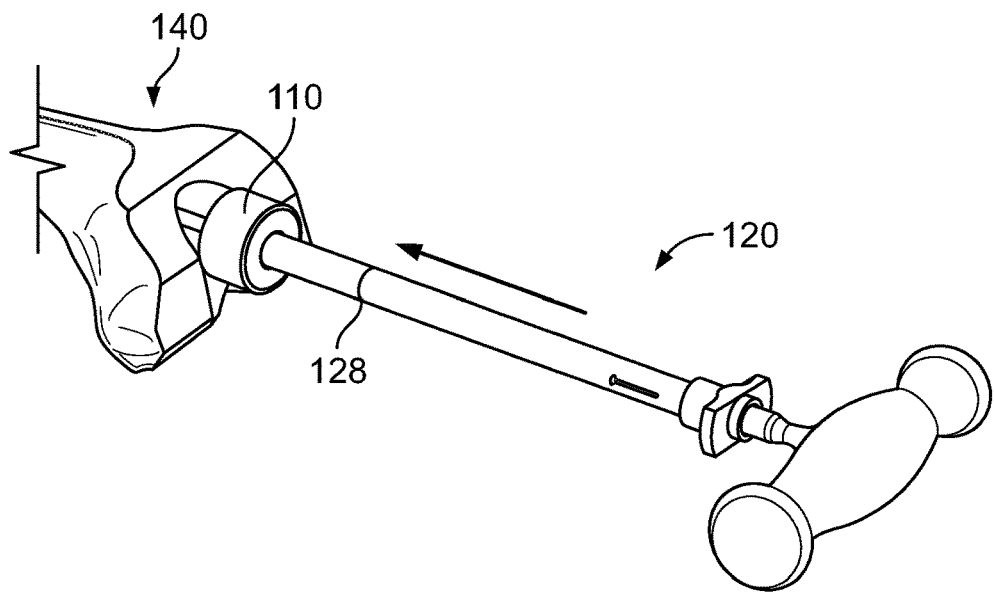
Figure 10C:
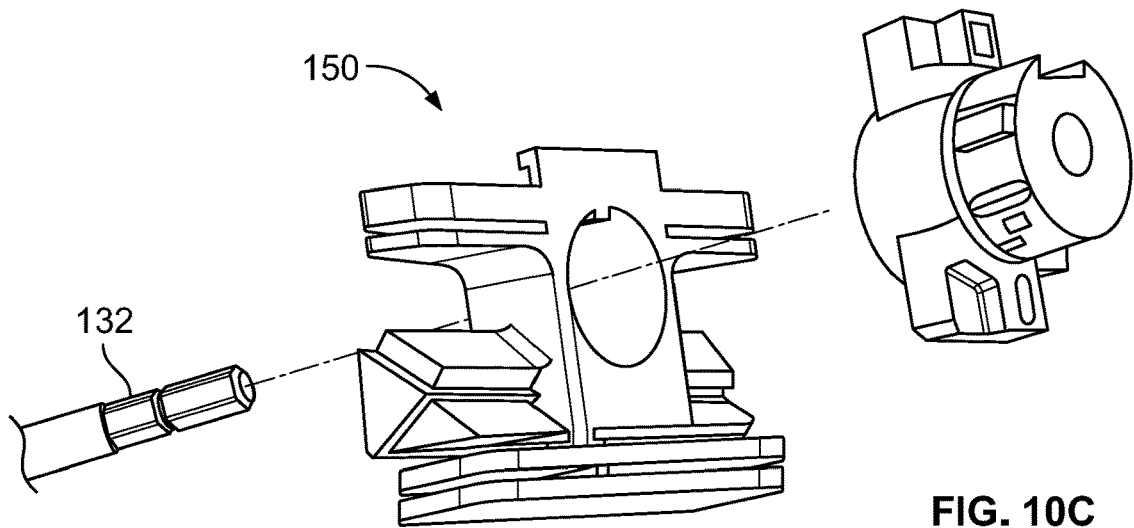

FIGS. 10A-10C depict a method of using stabilizer 110 and seating instrument 120 according to an embodiment of the present disclosure. In the method, a previously implanted prosthesis (not shown) may be removed from a bone 140, such as when the procedure is a revision arthroplasty. In this regard, an end of bone 140 may have previously resected bone surfaces 144 that may need to be further resected in preparation for a revision prosthesis. For instance, an intramedullary reamer 130 may be used to ream along the intramedullary canal of bone 140 which, as illustrated, is a femur. Of course, as noted above, procedures on other bones are also contemplated. Reamer 130 is left within the intramedullary canal so that a stem/shaft 132 of reamer 130 extends from an end of bone 140. However, due to bone loss or for other reasons, stem/shaft 132 may loosely fit within bone 140 so that it wobbles and/or sits out of alignment with the axis of bone 140. Stabilizer 110 may be used to help stabilize stem/shaft 132.

In order to use stabilizer 110, an opening/void 142 may be formed in the end of bone 140. In this regard, a cannulated reamer (not shown) may ream the end of bone 140 over stem/shaft 132 so as to form a conical or cylindrical opening 142 at the end of bone 140. Such void reamer may have a cutting head that corresponds to the outer dimension of stabilizer 110 so that when stabilizer 110 is placed within opening 142 formed by such reamer, stabilizer 110 snuggly fits against bone 140. Moreover, such void reamer may also be sized to correspond to a bone void prosthesis that may be implanted to create a support for a joint replacement prosthesis.

Once opening/void 142 is formed in bone 140, the void reamer is removed from stem/shaft 132. Thereafter, stabilizer 110 is placed over stem/shaft 132 such that stem/shaft 132 extends through hole 118 of stabilizer 110, as shown in FIG. 10A. Stabilizer 110 is pushed along stem/shaft 132 until it reaches opening/void 142. Seating instrument 120 is then placed over stem/shaft 132, as shown in FIG. 10B, until seating end 124 abuts first end 114 of stabilizer 110. Thereafter, seating instrument 120 is pushed within enough force to drive stabilizer 110 into the opening/void 142 until indicia 128 on shaft 122 aligns with an end of bone 140. Stabilizer 110 should snuggly fit within opening/void 142 so that it is held in position by opening/void 142. However, the fit should not be so tight that stabilizer 110 needs to be impacted into place. This could place excessive stress on bone 140 causing it to fracture. At this point, stabilizer 114 centers stem/shaft 132 and holds it in place so as to prevent it from moving off axis with bone 140.

Once stabilizer 110 is fully seated into position, seating instrument 120 is removed from stem/shaft 132. Other instrumentation can then be placed over stem/shaft 132 to perform other aspects of the procedure. For example, as shown in FIG. 10C, a cutting guide 150 may be placed over stem 132 while stabilized by stabilizer 110 so that bone 140 can be further resected via cutting guide 150 in order to receive a final prosthesis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of resecting an end of bone comprising:
   inserting a cutting guide having a guide surface into a void in an end of bone such that the guide surface is beneath an end surface of the bone; and
   resecting the bone along the guide surface while the cutting guide remains disposed within the void in the end of the bone.

2. The method of claim 1, further comprising connecting a cutting guide shim to a cutting guide body to form the cutting guide.

3. The method of claim 2, wherein the guide surface is disposed on the cutting guide shim.

4. The method of claim 3, further comprising connecting the cutting guide shim to the cutting guide body before the cutting guide body is inserted into the void.

5. The method of claim 4, further comprising connecting the cutting guide shim to the cutting guide body after the cutting guide body is inserted into the void.

6. The method of claim 1, further comprising:
   removing the cutting guide from the bone void after the cutting step, and
   inserting a void filler prosthesis into the void.

7. A method of preparing an end of bone to receive a prosthesis comprising:
   inserting a cutting guide having a cutting guide body and a cutting guide shim into a void in an end of bone;
   cutting the bone along a guide surface of the cutting guide shim while the cutting guide remains disposed within the void in the end of the bone so as to form a resected surface at the end of the bone;
   removing the cutting guide from the void; and
   implanting a void filler prosthesis into the void beneath the resected surface a distance equal to a thickness of the cutting guide shim.

8. The method of claim 7, wherein the cutting guide shim is threadedly connected to the cutting guide body via a right-handed threaded interface.

9. The method of claim 8, wherein the cutting guide is inserted into void via an inserter/extractor tool threadedly connected to the cutting guide shim, the inserter/extractor tool being threadedly connected to the cutting guide shim via a left-handed threaded interface.

\* \* \* \* \*